(12) United States Patent
Meyerhoff et al.

(10) Patent No.: US 6,339,102 B1
(45) Date of Patent: Jan. 15, 2002

(54) METHOD AND COMPOSITION FOR TREATING AND PREVENTING RETINAL DAMAGE

(75) Inventors: James Meyerhoff, Silver Spring, MD (US); Henry Hacker, Temple, TX (US); Michael L. Koenig, Silver Spring, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/590,174

(22) Filed: Jun. 9, 2000

Related U.S. Application Data

(60) Provisional application No. 60/138,273, filed on Jun. 9, 1999.

(51) Int. Cl.$^7$ .............................................. A61K 31/381
(52) U.S. Cl. ...................................... 514/438; 514/558
(58) Field of Search ............................. 514/357, 518, 514/558, 438

(56) References Cited

U.S. PATENT DOCUMENTS

| | | | | |
|---|---|---|---|---|
| 5,691,379 A | * | 11/1997 | Ulrich et al. | 514/557 |
| 5,747,545 A | * | 5/1998 | Lipton | 514/742 |
| 5,972,977 A | * | 10/1999 | Narducy et al. | 514/357 |
| 6,048,846 A | * | 4/2000 | Cochran | 514/168 |
| 6,103,756 A | * | 8/2000 | Gorsek | 514/458 |
| 6,107,315 A | * | 8/2000 | Carney et al. | 514/345 |

OTHER PUBLICATIONS

Stoyanovsky et al, Eye Res., vol. 14, #3, pp. 181–189 (abstreact), Mar. 1995.*
Kahler et al, Z. Gesamte. Inn. Med., vol. 48, #5, pp. 223–232 (abstract), May 1993.*

* cited by examiner

*Primary Examiner*—James H. Reamer

(57) ABSTRACT

The use of dihydrolipoic acid (DEL) and alpha-lipoic acid to treat and prevent damage to the retina arising from physical forces such as exposure to laser beams, and to compositions containing phenyl nitrones and DHL or alpha-lipoic acid as neuroprotective agents.

18 Claims, No Drawings

METHOD AND COMPOSITION FOR TREATING AND PREVENTING RETINAL DAMAGE

This application takes priority from Provisional Patent Application 60/138,273, filed Jun. 9, 1999.

FIELD OF THE INVENTION

This invention relates to use of dihydrolipoic acid (DHL) and a-lipoic acid to treat and prevent damage to the retina arising from physical forces such as exposure to laser beams, and to compositions containing phenyl nitrones and DHL or a-lipoic acid as neuroprotective agents.

BACKGROUND OF THE INVENTION

The retina is part of the central nervous system and contains both neurons and glia, as well as photo receptors.

Although the immediate mechanisms vary, many forms of neuro-trauma are believed to share a common final pathway: the formation of neurotoxic free radicals.

Individuals experiencing laser-induced retinal trauma often report seeing a bright flash of light at the time of the incident and subsequently notice impaired vision. Impairment of vision is often noticed immediately and may be documented early. Retinal injuries may either improve or worsen over time. Clinically observed signs range from hemorrhage (vitreous, pre-, post- or intra-retinal) to whitening (burn) of the retina. In later stages, puckering and/or perforation of the retina may occur. In such cases, further deterioration occurs over time. For example, in one soldier suffering from bilateral exposure, visual acuity in one eye declined from 20/50 twenty four hours post-injury to 20/100 over 6 months, subsequently deteriorating further to 20/400. The clinical course of the other eye was quite different. While maintaining 20/20 visual acuity over 14 months, a paracentral scotoma enlarged significantly as color vision and contrast sensitivity declined progressively. Decrements in dark adaptation are also reported. Therapeutic interventions included administration of steroids to control edema and inflammation and surgical interventions to remove blood from the vitreous or to manage retinal detachment or perforations.

Clinical features of injury to the retina via laser or other physical means include hemorrhage. Just as intracranial hemorrhage may cause hemosiderosis in the brain, bleeding into the retina appears to cause deposition of iron and resultant toxicity. It appears that laser-induced coagulation of retinal blood vessels causes local areas of retinal ischemia and hypoxia. Laser energy may also directly disrupt and traumatize retinal neurons. Whether due to ischemia or to direct acoustic and thermal trauma caused by the laser energy, it is likely that glutamate would be released as with any type of neurotrauma.

Alpha-lipoic acid ($\alpha$LA) is an antioxidant currently used clinically to treat diabetic neuropathy. It has been shown to be clinically safe and was shown to be neuro-protective against ischemia-perfusion injury in both the rat and the gerbil. It was also effective against NMDA and malonic acid lesions of striatum in rats. However, its effects in preventing or ameliorating damage to the retina, especially damage arising from physical trauma such as laser-induced damage, has not previously been considered.

Nitrone-based free radical traps offer an ROS scavenging mechanism which differs from vitamin E and other endogenous compounds. The nitrones react covalently with ROS to form stable nitroxides and as such they differ from endogenous scavengers such as the lipoic acids. They have also been shown to be neuroprotective against glutamate-induced toxicity in cultured neurons as well as in several rodent models of cerebral ischemia. In the rat focal ischemia model, they are neuroprotective even when initiation of treatment was delayed. One such compound is $\alpha$-Phenyl-N-tert-butylnitrone (PBN), which crosses the blood brain barrier, but has been found to be somewhat toxic in high concentrations. PBN was reported to attenuate the accumulation of lactate following cortical contusion in the rat. In the rat focal ischemia model, PBN was neuroprotective even when initiation of treatment was delayed as long as 12 hours. PBN, as well as other nitrones, also minimized seizures and delayed time to death in mice subjected to intracerebral lethal injection of ferrous chloride. A newer nitrone, N-tert-Butyl-$\alpha$-[2-sulfophenyl]-nitrone (SPBN), is also an effective neuroprotectant. SPBN (500 ng by intraocular injection) has been shown to rescue 27% of retinal ganglion cells after axotomy (Klocker et al., J. Neurosci. 18(3):1038-1046). SPBN ( 100 mg/kg i.p. 30 min prior and q 8 hours for 48 hours after insult; or 300 mg/kg, ip, 1 hours prior to insult and 0,1,2,3,6,9,12,18 & 24 hours after)is protective against striatal injections of NMDA, kainic acid, AMPA, MPP+, 3-acetyl pyridine and malonate, decreasing the volume of the lesions induced by those toxins, as well as decreasing malonate-induced formation of ROS.

Azulenyl nitrones were shown to be protective against ischemic injury in the gerbil and against MTPT in mice. Finally, another nitrone, NXY-059, was shown to be effective in both temporary and permanent focal ischemia models in the rat and was effective when given 3 hours or even 5 hours after start of recirculation in the former. In preliminary studies, NXY-059, administered either 15 minutes prior or 30 minutes post traumatic brain injury, was effective in decreasing volume of necrosis in the controlled cortical impact mode.

SUMMARY OF THE INVENTION

This invention provides methods for preventing or ameliorating damage to the retina by administration of retinal protective/healing amounts of $\alpha$-lipoic acid or dihydrolipoic acid in appropriate pharmaceutical carriers. The active agents may be administered systemically or topically.

The invention also provides improved compositions containing lipoic acids, including analogues of the acids, in combination with nitrones chosen from $\alpha$-Phenyl-N- tert-butylnitrone (PBN) and N-tertButyl-$\alpha$-[2-sulfophenyl]nitrone (SPBN) which will provide synergistic effects when used in combination for preventing and/or ameliorating damage to neurological tissue.

DETAILED DECSRIPTION OF THE INVENTION

The field of ophthalmology has concentrated on surgical or laser approaches to treatment. However, these approaches can cause damage to the retina. This invention involves use of $\alpha$-lipoic acid and dihydrolipoic acid as agents to protect from or to ameliorate retinal damage arising from physical trauma, including that arising from exposure to laser beams. These agents protect neurons via at least four mechanisms: (1) they are antioxidants; (2) they are recyclers of the antioxidant vitamins C and E; (3) they act as chelators of at least 8 species of free radicals; and (4) they increase intracellular energy stores (e.g. ATP). The $\alpha$-lipoic acid may be given orally and is readily absorbed and converted in the body to the more potent neuroprotectant, dihydrolipoic acid. Since α-LA is well-tolerated in man, it may be given prophylactically to persons such as military personnel that are at risk for laser-induced retinal injury. It may also be given prophylactically to patients who will be exposed to laser therapy or other sources of physical energy such as the bright lights used in surgery wherein the energy is directed at the eye or near-by organs. (Parafoveal laser injuries near central vision such as might be experienced by a pilot or ground soldier deliberately targeted by laser weaponry or accidental exposure to laser range finders cause particularly devastating results.) The administration of the α-LA or DHL would be continued after exposure to the trauma.

It is also possible to protect the retina from damage arising from disease conditions, whether systemic or ocular. Such diseases include diabetic retinopathy. Progressive diseases of the eye that might be treated using the active agents in accord with the teachings of this disclosure include, but are not limited to, macular degeneration, glaucoma, temporal arteritis and retinitis pigmentosa.

Cyanide-induced toxicity is mediated via inhibition of mitochondrial respiration and is a credible in vitro model for ischemia. To establish effectiveness of the methods described herein, the neuroprotective efficacy of DHL against cyanide-induced toxicity in retinal tissue in vitro was evaluated.

Materials and Methods

The N-tert-Butyl-α-[2-sulfophenyl]nitrone (SPBN) is listed in the Aldrich catalog where it is described as water-soluble.

EXAMPLE 1

Rabbits were anesthetized with $CO_2$ under a protocol approved by the institutional laboratory animal care and use committee (IACUC). The eyes were removed and the retinas dissected and placed in a chilled, oxygenated Locke's buffer (NaCl 154 mM, KCl 5.6 mM, $NaHCO_3$ 3.6 mM, and HEPES 0.5 mM) lacking Mg, glucose and calcium. The retinal tissue was then dissociated by mechanical trituration using pipettes of decreasing caliber. Measured aliquots of tissue were placed into 1.5 ml Eppendorf tubes and the buffer exchanged by pelletizing the cells at 500 g for 5 minutes. The supernatant was exchanged for modified Locke's buffer without Mg and glucose (NaCl 154 mM, KCl 5.6 mM, $NaHCO_3$ 3.6 mM, $CaCl$ 2.3 mM and HEPES 0.5 mM), which was used to resuspend the pellet to allow incubation of the cells under experimental conditions.

The tetrazolium dye (MTT) assay for succinate dehydrogenase (SDH) activity as used to determine viability of the dissociated cell preparation. Briefly, SDH in living cells converts to MTT, a calorimetric dye, into a blue formazan product that allows the absorbance of each specimen to be read by a photometric analyzer. The addition of MTT not only stains for viability at a given time, but also causes rapid demise of the cells once the formazan calorimetric endpoint is reached.

To assess the neuroprotective efficacy of dihydrolipoic acid (DHL), ischemic conditions were simulated by exposure of the cells to sodium cyanide (NaCN) and 2-deoxyglucose (2-DG). This model uses NaCN to inhibit oxidative metabolism and 2-DG to inhibit glycolysis. These conditions produce a rapid loss of ATP that allows for the rapid determination of the effect of these agents on viability. One set of speci- mens not exposed to NaCN and 2-DG was used as a control with respect to another set that were exposed to these insults. DHL was co-administered at two different concentrations, 0.1 and 0.3 millimolar. Values of treated versus untreated controls were compared using the Student's t-test for statistical significance.

Using NaCN and 2-DG to achieve approximately 60% toxicity in exposed cells, DHL provided significant protection against damage, with a maximum effect of approximately 60% at both concentrations tested ($p<0.004$, t-test) These data show that DHL significantly protects dissociated retinal cells against metabolic damage from NaCN and 2-DG. These results are consistent with the initial findings in cultured neurons.

When αLA is administered, it is readily taken up into the retina and is converted to DHL in vivo. The αLA can be administered chronically. Hence, either αLA or DHL would be useful against retinal damage and would be particularly useful when given prophylactically to persons exposed to retinal damage, whether the injury to tissue was caused by ischemia arising as a result of systemic disease such as arteriosclerosis or diabetes, from circumstances which result in ischemia-reperfusion, or from physical injury such as exposure to laser beams. These agents could also be used to protect against damage secondary to ocular trauma or glaucoma. Hence, compositions containing LA and/or DHL can be administered for long-term therapy and for prevention and treatment of temporary exposure to insult. Administration analogues such as esters or amides of lipoic acids may also be advantageous. Appropriate esters and amides, for example, include those commonly used as protective groups, and include, but are not limited to, alkyl, phenyl and phenylalkyl (including benzyl) substituted compounds. The ester moieties may substituted with, for example, alkyl, hydroxy, alkoxy and halo groups. An example of such a compound is the 2-(N,N-dimethylamine) ethylamido lipoate-HCL (LA-plus), which is disclosed by Tirosh, et al. (Free Rad. Biol & Med. 26(11/12):1418–1426, 1999.)

It has now been found that the neuroprotective properties of the antioxidant can be significantly enhanced, if it is supplemented with a nitrone such as the spin trap SPBN.

EXAMPLE 2

In a separate series of experiments, cultured neurons were pre-treated with four different concentrations of DHL with or without 10 mM SPBN for four hours. At the conclusion of the preincubation period, an oxidative insult was applied by adding 50 $\mu$M of hydrogen peroxide ($H_2O_2$) for an additional 30 min. Medium containing the $H_2O_2$ and antioxidants was then removed and Minimum Essential Medium (MEM) was added to the wells for 24 hours. Neuroprotection was then assessed by conducting the calorimetric MTT assay. One way ANOVA with significance of differences between means assessed by Tukey-Kramer Multiple Comparisons test.

SPBN significantly increased the neuroprotective efficacy of DHL at three of the four DHL concentrations tested. The combination of 100 $\mu$M DHL and 10 mM SPBN resulted in almost complete protection against $H_2O_2$-induced oxidative insult. Data are depicted as means±SEM (n=8). Significance was determined by one way ANOVA, and differences between the means was assessed by the Tukey-Kramer test. (See table 1).

TABLE 1

| Treatment | % Neuroprotection | n |
|---|---|---|
| DHL (3 μM) | 1.31 ± 5.23 | 8 |
| DHL (3 μM) + SPBN(10 mM) | 10.48 ± 3.04 | 8 |
| DHL (10 μM) | −3.68 ± 5.14 | 8 |
| DHL (10 μM) + SPBN(10 mM) | 44.51 ± 11.98 | 8 |
| DHL (30 μM) | 7.04 ± 7.38 | 8 |
| DHL (30 μM) + SPBN(10 mM) | 48.64 ± 6.09 | 7 |
| DHL (100 μM) | 28.48 ± 5.83 | 8 |
| DHL (100 μM) + SPBN(10 mM) | 86.44 ± 8.44 | 8 |

For protection from retinal damage, the active agents may be administered before, during and immediately after exposure to damage that may occur. Such instances include, but are not limited to, space travel, military involvement, eye surgery, or exposure to irradiation during treatment of conditions of the head and neck. The active agents may also be given on a more or less continuing basis to persons such as firefighters and welders who are constantly in danger of being exposed to conditions likely to cause retinal damage.

The active agents may be administered locally or systemically in pharmaceutically acceptable carriers such as isotonic saline or buffered saline, glucose in saline, etc. When given orally in capsule or tablet form, additional active agent inerts such as starches, sugars, flavoring agents and preservatives added. For local application, the αLA or DHL may also be administered as non-irritating ointments or salves. The active agents of the invention are relatively safe. Dosage range will depend on the method of administration and the age, size and condition of the patient. For example, 0.1 to 5 mM solutions of DHL may be administered parenterally. Capsules containing about 20 to 600 mg α-LA may be administered orally in capsule or tablet form. The preferred dosage range of α-LA is about 20 to 3000 mg/day. Appropriate dosage of DHL is about half that. For the average size individual, 20 to 1000 mg/day would be an appropriate dosage of α-LA. The dosage may most usually be delivered in 1–4 doses per day when given orally.

Compositions containing, in addition to α-lipoic acid, neuroprotective amounts of α-Phenyl-N-tert-butylnitrone or N-tert-Butyl-α-[2-sulfophenyl]nitrone, would deliver 0.1–100 mg/kg/day in a mammal, with about 1–100 mg/kg/day being more appropriate for administration to larger mammals such as man.

EXAMPLE 3

A composition for oral administration is suggested
α-lipoic acid 25 mg
N-tert-Butyl-α-[2-sulfophenyl]nitrone (SPBN) 100 mg
Starch 375 mg

EXAMPLE 4

Composition for parenteral administration
DHL 10 mg
N-tert-Butyl-α-[2-sulfophenyl]nitrone (SPBN) 100 mg
Saline sufficient to provide 5 ml.
This composition may be administered parenterally or as drops to the eye before or after exposure to laser beams.

Compositions such as salves or ointments may also be used and may contain, additionally, antibotics, analgesics, etc.

The N-tert-Butyl-α-[2-sulfophenyl]nitrone (SPBN) is the preferred nitrone for use in the methods of the invention.

Though PBN is neuroprotective, toxicity is a problem if this agent is used in very high doses.

What we claim is:

1. A method of preventing retinal damage by administration of a retinal-protective effective amount of α-lipoic acid or esters or amides of the lipoic acid in a pharmaceutically acceptable carrier.

2. A method of claim 1 wherein a nitrone is administered concurrently with the α-lipoic acid.

3. A method of claim 1 wherein α-lipoic acid is administered prophylactically by mouth.

4. A method of claim 3 wherein α-lipoic acid is administered concurrently with N-tert-Butyl-α-[2-sulfophenyl]-nitrone (SPBN).

5. A method of claim 1 wherein α-lipoic acid is administered chronically to persons likely to be exposed to irradiation or laser beams.

6. A method of claim 4 wherein the α-lipoic acid and N-tert-Butyl-α-[2-sulfophenyl]nitrone (SPBN) are administered prophylactically to persons likely to be exposed to irradiation or laser beams.

7. A method of claim 5 wherein the α-lipoic acid is administered by mouth.

8. A method of claim 7 wherein the composition administered contains α-lipoic acid and N-tert-Butyl-α-[2-sulfophenyl]nitrone (SPBN).

9. A method of claim 1 wherein the patient suffers from systemic disease which may damage the retina.

10. A method of claim 7 wherein α-lipoic acid is administered chronically by mouth.

11. A method of claim 8 wherein α-lipoic acid and N-tert-Butyl-α-[2-sulfophenyl]nitrone (SPBN) are administered chronically by mouth.

12. A method of treating individuals who have been exposed to retinal-damaging amounts of trauma comprising administration of retinal-healing effective amounts of α-lipoic acid in a pharmaceutically acceptable carrier.

13. A method of claim 12 wherein, in addition to α-lipoic acid, there is administered concurrently a nitrone chosen from α-Phenyl-N-tert-butylnitrone (PBN) and N-tert-Butyl-α-[2-sulfophenyl]nitrone (SPBN).

14. A method of claim 13 wherein there is administered a composition containing α-lipoic acid and N-tert-Butyl-α-[2-sulfophenyl]nitrone (SPBN).

15. A method of claim 12 wherein α-lipoic acid is administered orally.

16. A method of treating individuals who have been exposed to retinal-damaging amounts of trauma comprising administration of retinal-healing effective amounts of dihydrolipoic acid in a pharmaceutically acceptable carrier systemically.

17. A method of claim 16 wherein, in addition to dihydrolipoic acid, the composition administered parenterally contains N-tert-Butyl-α-[2-sulfophenyl]nitrone (SPBN).

18. A composition of matter comprising a retinal-protective amount of α-lipoic acid or esters or amides of lipoic acid and a neuroprotective amount of at least one agent chosen from α-Phenyl-N-tert-butylnitrone (PBN) and N-tert-Butyl-α-[2-sulfophenyl]nitrone (SPBN).

* * * * *